(12) United States Patent
Ohno et al.

(10) Patent No.: US 7,520,178 B2
(45) Date of Patent: Apr. 21, 2009

(54) METHOD FOR INSPECTING HONEYCOMB FIRED BODY AND METHOD FOR MANUFACTURING HONEYCOMB STRUCTURED BODY

(75) Inventors: Kazushige Ohno, Ibi-gun (JP); Koji Shimato, Dunavarsany (HU); Norihiko Yamamura, Ibi-gun (JP)

(73) Assignee: Ibiden Co., Ltd., Ogaki-shi (JP)

( * ) Notice: Subject to any disclaimer, the term of this patent is extended or adjusted under 35 U.S.C. 154(b) by 0 days.

(21) Appl. No.: 11/749,961

(22) Filed: May 17, 2007

(65) Prior Publication Data

US 2008/0115597 A1 May 22, 2008

Related U.S. Application Data

(63) Continuation of application No. PCT/JP2006/308343, filed on Apr. 20, 2006.

(51) Int. Cl.
*G01N 19/08* (2006.01)
(52) U.S. Cl. .......................................................... 73/799
(58) Field of Classification Search .................. None
See application file for complete search history.

(56) References Cited

U.S. PATENT DOCUMENTS

| | | | |
|---|---|---|---|
| 6,945,111 B2 * | 9/2005 | Georgeson | 73/600 |
| 7,315,609 B2 * | 1/2008 | Safai et al. | 378/57 |
| 2003/0142298 A1 | 7/2003 | Ujihara et al. | |
| 2004/0007077 A1 * | 1/2004 | Hijikata | 73/799 |
| 2005/0214503 A1 * | 9/2005 | Sakamoto | 428/116 |
| 2006/0029897 A1 | 2/2006 | Saijo et al. | |
| 2006/0029898 A1 | 2/2006 | Saijo et al. | |
| 2006/0043652 A1 | 3/2006 | Yamada | |
| 2006/0073970 A1 | 4/2006 | Yamada | |
| 2006/0108347 A1 | 5/2006 | Koyama et al. | |
| 2006/0118546 A1 | 6/2006 | Saijo | |
| 2006/0169384 A1 | 8/2006 | Fujita et al. | |
| 2006/0245465 A1 | 11/2006 | Saijo et al. | |
| 2006/0269722 A1 | 11/2006 | Yamada | |
| 2007/0085233 A1 | 4/2007 | Yamada | |
| 2007/0144561 A1 | 6/2007 | Saijo et al. | |
| 2007/0148403 A1 | 6/2007 | Yamamura et al. | |
| 2007/0152382 A1 | 7/2007 | Yamada | |
| 2007/0262498 A1 | 11/2007 | Saijo et al. | |
| 2008/0067725 A1 | 3/2008 | Naruse et al. | |
| 2008/0084010 A1 | 4/2008 | Naruse et al. | |
| 2008/0088072 A1 | 4/2008 | Kobayashi | |
| 2008/0106008 A1 | 5/2008 | Kasai et al. | |
| 2008/0106009 A1 | 5/2008 | Naruse et al. | |
| 2008/0116200 A1 | 5/2008 | Kawai et al. | |
| 2008/0136053 A1 | 6/2008 | Kuribayashi et al. | |
| 2008/0150200 A1 | 6/2008 | Tajima | |

(Continued)

FOREIGN PATENT DOCUMENTS

EP 0 445 962 5/1996

(Continued)

*Primary Examiner*—Robert R Raevis
(74) *Attorney, Agent, or Firm*—Ditthavong Mori & Steiner, P.C.

(57) ABSTRACT

A method for inspecting a honeycomb fired body includes transporting the honeycomb fired body along a transportation line, and inspecting the honeycomb fired body for a crack during the transporting step.

27 Claims, 7 Drawing Sheets

U.S. PATENT DOCUMENTS

2008/0157445 A1 7/2008 Kawai et al.
2008/0160249 A1 7/2008 Makino

FOREIGN PATENT DOCUMENTS

| EP | 0 412 513 | 6/1996 |
| EP | 1 380 830 | 12/2005 |
| EP | 1 825 900 | 8/2007 |
| JP | 5-034558 | 5/1993 |
| JP | 2003-207472 | 7/2003 |
| JP | 2003-222595 | 8/2003 |
| JP | 2004-045276 | 2/2004 |
| JP | 2004-261625 | 9/2004 |

* cited by examiner

A-A line cross-sectional view

US 7,520,178 B2

METHOD FOR INSPECTING HONEYCOMB FIRED BODY AND METHOD FOR MANUFACTURING HONEYCOMB STRUCTURED BODY

CROSS-REFERENCE TO RELATED APPLICATIONS

The present application claims priority under 35 U.S.C. §120 to PCT Application No. PCT/JP2006/308343, filed Apr. 20, 2006, entitled "METHOD FOR INSPECTING HONEYCOMB FIRED BODY AND METHOD FOR MANUFACTURING HONEYCOMB STRUCTURED BODY." The contents of this application are incorporated herein by reference in their entirety.

BACKGROUND OF THE INVENTION

1. Field of the Invention

The present invention relates to a method for inspecting a honeycomb fired body and a method for manufacturing a honeycomb structured body.

2. Discussion of the Background

In recent years, particulates such as soot contained in exhaust gases that are discharged from internal combustion engines of vehicles, such as buses and trucks, and construction machines, have raised serious problems as contaminants harmful to the environment and the human body.

Various honeycomb filters using honeycomb structured bodies made from porous ceramic materials, which serve as filters that capture particulates in exhaust gases to purify the exhaust gases, have been proposed.

Conventionally, upon manufacturing a honeycomb structured body, first, ceramic powder and a binder are dry-mixed, and to this is further added a dispersant solution, and mixed so that a wet mixture is prepared. Then, the wet mixture is continuously extrusion-molded through a die, and the extruded molded body is cut into a predetermined length so that a pillar-shaped honeycomb molded body is manufactured.

Next, the resulting honeycomb molded body is dried, and predetermined cells are sealed so as to manufacture a honeycomb molded body in which one of ends of each cell is sealed with a plug material layer, and thereafter, a degreasing process and a firing process are carried out on the honeycomb molded body so that a honeycomb fired body is manufactured.

Thereafter, a sealing material paste is applied to the side faces of each of the honeycomb fired bodies, and the honeycomb fired bodies are combined with one another to manufacture an aggregate of the honeycomb fired bodies in which a number of honeycomb fired bodies are combined with one another by interposing sealing material layers (adhesive layers). Next, the resulting aggregate of the honeycomb fired bodies is cut and machined into a predetermined shape such as a cylindrical shape and a cylindroid shape by using a cutting tool or the like to form a ceramic block, and lastly, a sealing material paste is applied onto the outer periphery of the ceramic block to form a sealing material layer (coat layer); thus, a honeycomb structured body is manufactured, and then an inspection is carried out on the honeycomb structured body thus manufactured, thereby completing the manufacturing of the honeycomb structured body.

In the present specification, in any of the forms of the honeycomb molded body, honeycomb fired body and honeycomb structured body, those faces to which cells are exposed, among faces that form the respective external shapes, are referred to as end faces, and those faces other than the end faces are referred to as side faces.

Here, with respect to the inspection method to determine whether or not a honeycomb structured body has a crack, there have been proposed a method for detecting a crack on the surface of a honeycomb structured body in which a temperature gradient is generated in the honeycomb structured body to measure the surface temperature distribution so that a crack is detected by conducting a predetermined image processing on the resulting temperature distribution; and a crack detection method for a honeycomb structured body in which the honeycomb structured body is placed with its end faces facing up and down on a mounting face, and applied thereto an impact load so much as to allow powder matters to drop from a portion having a crack, so that a crack is detected by detecting the dropped powder matters. See, for example, Japanese Unexamined Patent Application Publication No. 2003-207472 and Japanese Unexamined Patent Application Publication No. 2004-45276. The contents of JP-A 2003-207472 and JP-A 2004-45276 are incorporated herein by reference in their entirety.

SUMMARY OF THE INVENTION

According to one aspect of the present invention, a method for inspecting a honeycomb fired body includes transporting the honeycomb fired body along a transportation line, and inspecting the honeycomb fired body for a crack during the transporting step.

According to another aspect of the present invention, a method for manufacturing a honeycomb structured body includes molding a ceramic material to form a plurality of honeycomb molded bodies, firing the plurality of the honeycomb molded body to make a plurality of honeycomb fired bodies, inspecting the plurality of the honeycomb fired bodies for a crack, and making the honeycomb structured body using a honeycomb fired body without a crack among the plurality of the honeycomb fired bodies.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
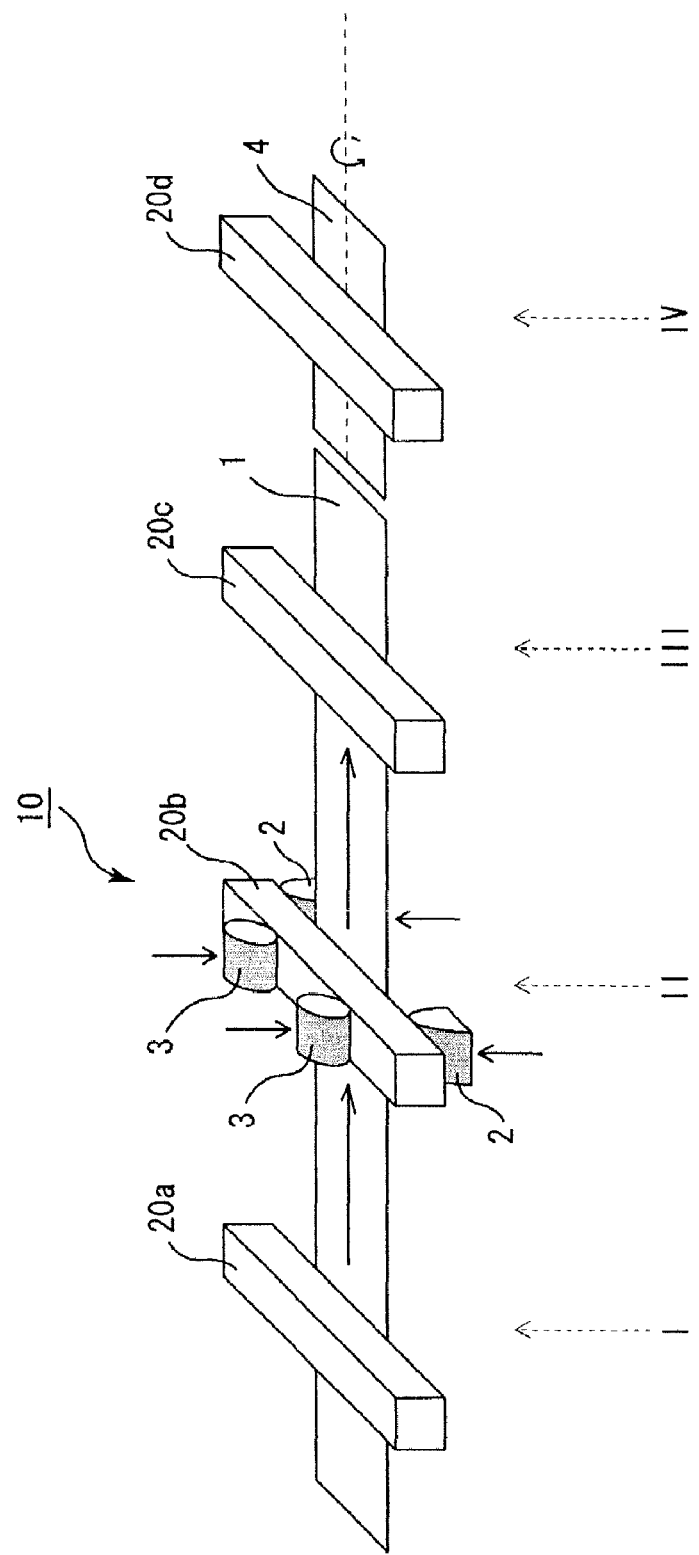
FIG. 1 is a perspective view of an inspection device which is used in a method according to an embodiment of the present invention.

The embodiments will now be described with reference to the accompanying drawings, wherein like reference numerals designate corresponding or identical elements throughout the various drawings.

First, referring to the drawings, the following description will discuss the method for inspecting a honeycomb fired body according to an embodiment of the present invention. The method for inspecting a honeycomb fired body according to an embodiment of the present invention comprises inspecting the presence or absence of a crack in a pillar-shaped honeycomb fired body having a number of cells longitudinally placed in parallel with one another with a cell wall therebetween, while the honeycomb fired body is being transported by a transporting member.

The subject to be inspected by the method for inspecting a honeycomb fired body of according to an embodiment the present invention is not particularly limited as long as it is a pillar-shaped honeycomb fired body that has been fired, and examples of the subject to be inspected include a rectangular pillar-shaped honeycomb fired body such as that as shown in FIG. 4(a), a cylindrical honeycomb fired body and the like, each having a number of cells penetrating in the longitudinal direction.

In the present specification, the shape indicated by the word "pillar" refers to any desired shape of a pillar including a round pillar, an oval pillar, a polygonal pillar and the like.

Moreover, the cracks in the honeycomb fired body include not only so-called fine cracks in the honeycomb fired body caused by an impact or uneven temperature distributions and the like upon firing, but also so-called pin holes, which are caused by continuous or discontinuous pores that have existed before and after the firing process and remain, as they are, even after the firing process.

FIG. 1 is a perspective view of an inspection device which is used in a method according to an embodiment of the present invention. In the method for inspecting a honeycomb fired body according to an embodiment of the present invention, inspection for the presence or absence of a crack in the honeycomb fired body is carried out while the honeycomb fired body is being transported by a transporting member. As shown in FIG. 1, honeycomb fired bodies 20a, 20b, 20c and 20d, which have been transported from the preceding process, are successively transported by a transporting member 1. When the honeycomb fired body 20, transported by the transporting member 1, has reached a position of an inspection unit 10, the transporting member 1 once stops the transportation for inspection in the inspection unit 10. In the inspection unit 10, the honeycomb fired body is inspected for the presence or absence of a crack, and after the completion of the inspection, it is again transported by the transporting member 1, and sent to the next process.

In the inspection unit 10 shown in FIG. 1, a four-point bending strength test (which will be described later) is adopted as its inspection method. The inspection method may include a three-point bending strength test and other tests having the same effects. On the lower face of the honeycomb fired body 20b, supporting members 2 support portions of the honeycomb fired body 20b near the two ends thereof, and on the other hand, a pressing member 3 imposing a predetermined load is pressed onto the upper face of the honeycomb fired body 20b.

Here, the honeycomb fired bodies which have been determined as good products, that is, the honeycomb fired bodies having no cracks, through the crack inspection in the inspection unit 10, are directly transported to the next process to carry out treatments thereon. In contrast, the honeycomb fired bodies which have been determined as defective products, that is, the honeycomb fired bodies having a crack through the crack inspection, are excluded from the transporting line by a distribution mechanism 4 without being sent to the next process, and disposed of and the like properly.

Figure 7:
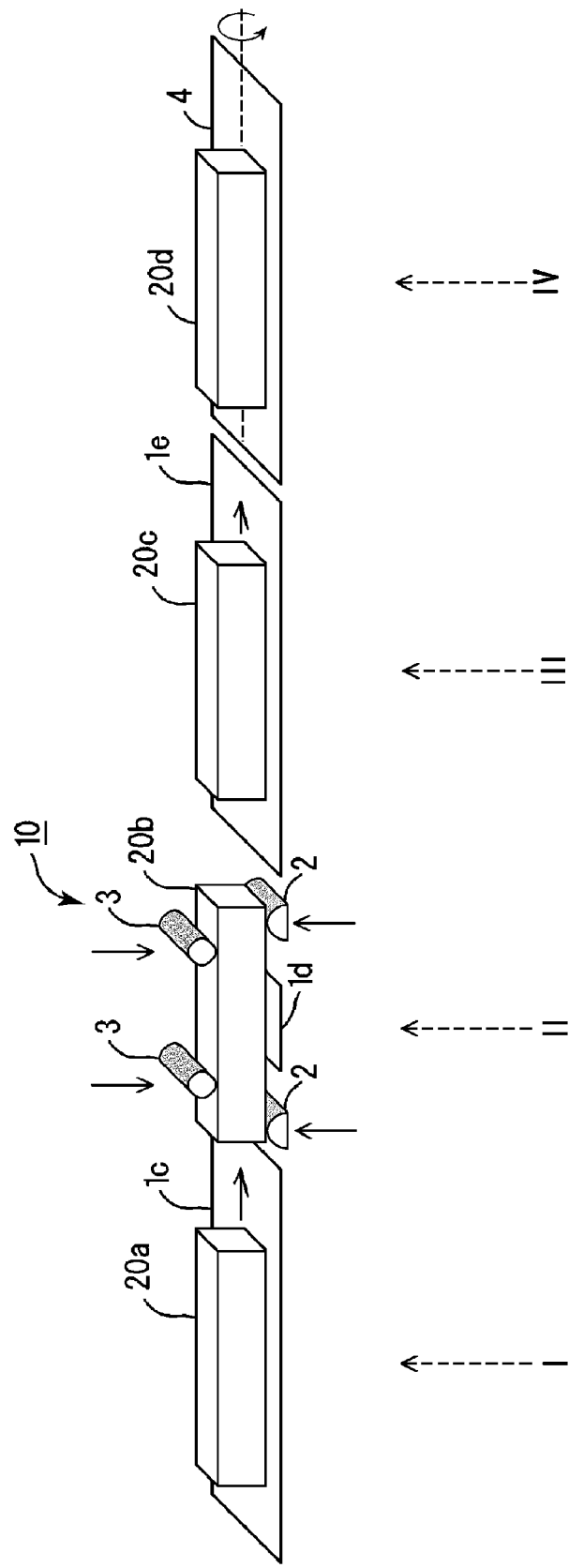
FIG. 7 is a perspective view of an inspection device which is used in a method according to a further embodiment of the present invention.

The honeycomb fired body may be placed on the transporting member 1 with its longitudinal direction substantially perpendicular to the transporting direction of the transporting member 1 as shown in FIG. 1, or may be placed with its longitudinal direction substantially in parallel with the transporting direction as shown in FIG. 7 with transporting members 1c, 1d, and 1e. The layout direction of the honeycomb fired body on the transporting member 1 may be properly altered depending on the inspection method in the inspection unit 10; however, when the layout space and the transporting efficiency are taken into consideration, it is preferable to place the honeycomb fired body with its longitudinal direction substantially perpendicular to the transporting direction.

The transporting member 1 is used, for example, for transporting a honeycomb fired body 20 from the preceding process such as a cooling process for cooling a honeycomb fired body obtained after firing of a honeycomb molded body to the next process in which a predetermined process is carried out by using the honeycomb fired body and/or on the honeycomb fired body. The transporting member 1 is not particularly limited, as long as it can transport the honeycomb fired body 20, and examples thereof include: a conveyor such as a belt conveyor and a chain conveyor, a cart that travels on rails, and the like.

With respect to the contact face of the transporting member 1 to the honeycomb fired body 20, the material for the contact face is not particularly limited as long as it does not damage the surface of the honeycomb fired body 20, and examples thereof include rubber such as natural rubber and synthetic rubber, and resin such as an urethane resin.

Although not particularly limited, the transporting speed of the transporting member 1 upon transporting the honeycomb fired body 20 is desirably at least about 5 m/min and at most about 40 m/min.

The transporting speed of less than about 5 m/min causes a reduction in the productivity, because much time is required just for transporting the honeycomb fired body; in contrast, the transporting speed exceeding about 40 m/min imposes an excessive load on the transporting member 1 that repeats the transporting and stopping operations, resulting in a possible failure in the transporting process.

In the case where the honeycomb fired body 20 is placed on the transporting member 1 in such a manner that the longitudinal direction of the honeycomb fired body 20 is orthogonal to the transporting direction of the transporting member 1, the width of the transporting member 1 may be longer or shorter than the longitudinal length of the honeycomb fired body 20. The width of the transporting member 1 can be properly adjusted depending on the inspection method used in the inspection unit 20; however, in the case where a three-point bending strength test or a four-point bending strength test is carried out as shown in FIG. 1, the width of the transporting member 1 is desirably made shorter than the longitudinal length of the honeycomb fired body 20 so as to carry out the test efficiently.

The transporting operation of the transporting member 1 may be conducted continuously, or may be conducted intermittently, depending on the inspection method used in the inspection unit 10. For example, in the case of a contact inspection such as four-point bending test, the transporting operation of the honeycomb fired body may be conducted intermittently, and on the other hand, in the case of a non-contact inspection such as X-ray inspection, the honeycomb fired body may be transported continuously.

In the method for inspecting a honeycomb fired body according to an embodiment of the present invention, the transporting member 1 is provided with a distribution mechanism 4, and those honeycomb fired bodies having no cracks and those honeycomb fired bodies having a crack are desirably separated by the distribution mechanism 4.

As shown in FIG. 1, the distribution mechanism 4, which separates honeycomb fired bodies depending on the presence or absence of a crack, is placed in parallel with the transporting member 1 on the downstream side of the transporting member 1 in the transporting direction. When the transporting member 1 is provided with the distribution mechanism 4 in this manner, those honeycomb fired bodies having no cracks (hereinafter, those honeycomb fired bodies having no cracks are referred to also as good honeycomb fired bodies) and those honeycomb fired bodies having a crack (hereinafter, those honeycomb fired bodies having a crack are referred to also as defective honeycomb fired bodies) can be efficiently separated, without disconnecting, in midstream, the transporting line of the honeycomb fired body 20, directed from one process to another process.

Referring to FIG. 1, the following description will discuss specific structure and operations of the transporting member 1 provided with the distribution mechanism 4. As shown in FIG. 1, the position of a honeycomb fired body 20a prior to the inspection is indicated by position I; the position of a honeycomb fired body 20b to be inspected in the inspection unit 10 is indicated by position II; the position of a honeycomb fired body 20c that is being transported after the inspection is indicated by position III; and the position of a honeycomb fired body 20d placed on the distribution mechanism 4 is indicated by position IV.

The four honeycomb fired bodies 20a, 20b, 20c and 20d are placed on the transporting member 1 or the distribution mechanism 4 at equal intervals, and each of the honeycomb fired bodies is transported to the position of the adjacent honeycomb fired body on the side in the transporting direction by one transporting operation of the transporting member 1 and the distribution mechanism 4. In other words, by the one transporting operation, the honeycomb fired body 20a at the position I is transported to the position II, and the honeycomb fired body 20b is simultaneously transported to the position III. In the same manner, the honeycomb fired body 20c at the position III is transported to the position IV on the distribution mechanism 4. By repeating those operations, the honeycomb fired bodies can be transported intermittently through a so-called assembly line operation.

Here, in the case where the inspection method in the inspection unit 10 is a non-contact inspection method without the necessity of temporarily stopping the transportation of the transporting member 1, the honeycomb fired bodies may be transported continuously.

Here, the transporting member 1 and the distribution mechanism 4 may have the same structure or different structures. Supposing that the transporting member 1 is a belt conveyor and that the distribution mechanism 4 is also a belt conveyor, the following description will discuss the structure of the distribution mechanism 4.

The distribution mechanism 4, however, is not necessarily a belt conveyor, and may be a transporting mechanism as exemplified in the description of the transporting member 1. In addition to this, the distribution mechanism 4 may have another structure in which, in transporting paths branched into a "Y" shape on the downstream side in the transporting direction, a discrimination arm is placed on the branched portion of the branched paths so that honeycomb fired bodies after the inspection are distributed onto a good product transporting path used for transporting honeycomb fired bodies having no cracks or a defective product transporting path used for transporting honeycomb fired bodies having a crack by this discrimination arm.

First, the following description will discuss a case in which the honeycomb fired body 20d is determined as a product having no cracks (good product) in the inspection unit 10.

After the inspection in the inspection unit 10, the honeycomb fired body 20d determined as a good product, which has been transported to the distribution mechanism 4 by the transporting member 1, is further transported to the position IV by the transporting operation of the distribution mechanism 4. Here, since the honeycomb fired body 20d on the distribution mechanism 4 has been determined as a good product in the inspection unit 10, the distribution mechanism 4 again starts the transporting operation so that the honeycomb fired body 20d determined as a good product is directly transported to the next process.

As the honeycomb fired body 20d is transported to the next process, the honeycomb fired body 20c after the inspection, the honeycomb fired body 20b at the inspection unit 10 and the honeycomb fired body 20a prior to the inspection are transported to the position IV, position III and position II, respectively.

Next, the following description will discuss a case in which the honeycomb fired body 20d is determined as a product having a crack (defective product) in the inspection unit 10.

After the inspection, the honeycomb fired body 20d, which is a defective product, is transported to the position IV by the transporting operation of the transporting member 1 and the distribution mechanism 4. When the defective honeycomb fired body 20d has been transported to the position IV, the distribution mechanism 4 rotates centering around a hypothetical broken line in the direction of an arrow shown in FIG. 1 so that the defective honeycomb fired body 20d is excluded by dropping off and the like from the transporting line. The defective honeycomb fired body thus excluded from the transporting line is then disposed of by a predetermined method.

The excluding process of the defective honeycomb fired body 20d from the transporting line may be carried out during the inspection process of the honeycomb fired body 20b in the inspection unit 10. In other words, when the inspection for a crack in the honeycomb fired body 20b transported to the inspection unit 10 is carried out, concurrently the defective honeycomb fired body 20d is excluded from the transporting line by the distribution mechanism 4. The following description will discuss this flow of transporting processes of the honeycomb fired body.

Since the honeycomb fired body 20d is a defective product as described above, the distribution mechanism 4 rotates to exclude the honeycomb fired body 20d from the transporting line, and in parallel with this operation, the inspection unit 10 carries out an inspection on the honeycomb fired body 20b so as to determine the presence or absence of a crack. Next, the transporting operations of the transporting member 1 and the distribution mechanism 4 are carried out so that the honeycomb fired body 20c (which has been already determined as a good product in the inspection unit 10) is transported to the position IV on the distribution mechanism 4, while the honeycomb fired body 20b, which has been inspected, is transported to the position III. In the same manner, the honeycomb fired body 20a prior to the inspection is transported to the inspection unit 10 at the position II so as to be inspected.

Since the honeycomb fired body 20c, transported to the position IV on the distribution mechanism 4, is a good product, it is transported directly to the next process by the next transporting operation of the distribution mechanism 4, and in parallel with this, the honeycomb fired body 20b after the inspection, located at position II, is transported to position IV on the distribution mechanism 4. In the same manner, the honeycomb fired body 20a after the inspection in the inspection unit 10 is transported to position II. Then, a new honeycomb fired body, not shown, is transported to position I.

In the embodiment of the present invention shown in FIG. 1, as has been explained, the transporting member 1 and the distribution mechanism 4 each carry out transporting operations twice during a period from the determination of the presence or absence of a crack in the inspection unit 10 to the transportation of the honeycomb fired body to the distribution mechanism 4 for distribution (that is, from the position II to the position IV). However, the number of times of the transporting operations required for transporting the honeycomb fired body from the inspection unit 10 to the distribution mechanism 4 is not limited to twice, and may be once, or three or more times. For example, with respect to the mode of transporting the honeycomb fired body through one transporting operation, the honeycomb fired body may be directly transported from the position II to the position IV without including stoppage of the transporting operation when the honeycomb fired body has reached the position III. Moreover, for transporting the honeycomb fired body from the position II to the position IV through transporting operations of three or more times, a new stoppage position may be included in addition to the position III. In this manner, the number of times of the transporting operations may be appropriately changed by taking the size of the transporting line, the production efficiency and the like into consideration.

The transporting member 1 provided with the distribution mechanism 4 repeatedly carries out these transporting operations so that the inspection for the presence or absence of a crack can be carried out on the transporting line, and good products and defective products of the honeycomb fired bodies can be positively discriminated, as well as inspection for the presence or absence of a crack in honeycomb fired bodies can be determined on the transporting line; therefore, it becomes possible to conduct a total inspection on the manufactured honeycomb fired bodies without causing a reduction in the production efficiency.

Next, the following description will discuss the inspection method used in the inspection unit 10.

With respect to the inspection method for inspecting cracks in the inspection unit 10, various methods may be adopted, and examples thereof include: a method in which inspection of honeycomb fired bodies is carried out by applying a predetermined load thereto, a hammering method utilizing a sound generated upon hitting honeycomb fired bodies, a method of detecting cracks based upon differences of the temperature distribution obtained when honeycomb fired bodies are heated, a method in which an X-ray image of honeycomb fired bodies is taken by applying X-rays thereto, a method of detecting cracks by utilizing vibration caused upon application of ultrasonic waves, a method in which a gas is allowed to flow through honeycomb fired bodies so as to detect gas leakage, a method in which electrodes are inserted into the cells so as to detect a current conduction between the cells, and the like.

The inspection for the presence or absence of a crack is desirably carried out by applying a predetermined load onto the honeycomb fired body.

This method is preferable because even a fine crack has a great influence on the mechanical strength of the honeycomb fired body so that the change in the mechanical strength is favorably correlated with the presence or absence of a crack, and because the inspection can be carried out by simply applying a load onto a subject to be inspected, this method can be widely applied regardless of the material, shape and the like of the subject to be inspected.

Moreover, since this method requires only a short period of time for the inspection, it is not necessary to prepare a plurality of inspection units in parallel, and therefore, the inspection can be carried out efficiently.

Furthermore, since fine cracks can be detected by this method, high inspection accuracy can be achieved.

In the embodiment of the present invention, determination of good products or defective products is made not based on the strength of the honeycomb fired body obtained in a manner that a load imposed on the honeycomb fired body up to its fracture is directly measured so as to define the measured value as the strength of the honeycomb fired body, but based on the presence or absence of a crack in the honeycomb fired body after a predetermined load is applied to the honeycomb fired body. In other words, the predetermined load applied to the honeycomb fired body is a load by which, upon carrying out a load imposing test such as a three-point bending test or a four-point bending test, the corresponding honeycomb fired body would be fractured if a crack existed therein.

With respect to the method for inspecting the presence or absence of a crack by applying a predetermined load, although not particularly limited, an example includes a commonly used method using a three-point bending test or a four-point bending test. In the embodiment of the present invention, upon evaluation of the mechanical strength, an inspection system for intermittently evaluating the strength is desirably used.

The following description will discuss the system of a four-point bending test which is modified so as to intermittently measure the mechanical strength of a honeycomb fired body as an example of the method for inspecting the presence or absence of a crack by applying a predetermined load to the honeycomb fired body.

As shown in FIG. 1, two supporting members 2 and two pressing members 3 are installed in the inspection unit 10, and a detection device, not shown, for detecting the existence of a honeycomb fired body 20b is also installed therein. When the detection device recognizes that the honeycomb fired body 20b has reached the position II at which the supporting members 2 are installed, the transporting operation of the transporting member 1 is once stopped, and the two supporting members 2 are made in contact with positions near the two ends of the honeycomb fired body 20b to lift and support the honeycomb fired body 20b. Each of the two supporting members 2 is machined so as to have a reversed "V" shape or a reversed "U" shape in its cross section; thus, the lower face of the honeycomb fired body 20b linearly contacts with the upper portions of the supporting members so that the honeycomb fired body 20b is supported at the linearly contacted portions.

Next, the two pressing members 3 are descended toward the upper face of the honeycomb fired body 20b supported by the supporting members 2 to be made in contact therewith. Here, as described above, the load to be applied is a load by which a fracture occurs in the corresponding honeycomb fired body if a crack existed therein. Here, in a reversed manner as the supporting members 2, the lower portion of each of the pressing members 3 is machined into a "V" shape or a "U" shape in its cross section so that the upper face of the honeycomb fired body 20b linearly contacts with the lower portion of each of the pressing member 3; thus, the honeycomb fired body 20b is pressed at the linearly contacted portions.

Thereafter, a predetermined load is applied to the honeycomb fired body 20b through the pressing members 3, and inspection for the presence or absence of a crack is carried out. In the case where, upon applying a predetermined load by the pressing members 3, the honeycomb fired body 20b is fractured or a large crack or the like, which can be visually confirmed, is caused therein, the honeycomb fired body 20b is determined as having a crack. In contrast, in the case where no abnormality such as a fracture is confirmed in the honeycomb fired body 20b, the honeycomb fired body 20b is determined as having no cracks. The determination as to the presence or absence of a crack in the inspection unit 10 is carried out by a load detector, not shown, which detects a change in the load (for example, an incidence of a sudden drop in the load that has increased in a fixed proportion, and the like) when the honeycomb fired body is fractured and the like by the applied load.

In the present specification, a honeycomb fired body without a crack or without cracks is defined as a honeycomb fired body that has substantially no cracks, and the honeycomb fired body without a crack or without cracks may include a honeycomb fired body which contains a crack in such a degree as not to cause adverse effects to the quality even when it is used as a product.

When, as a result of inspection at the inspection unit 10, the honeycomb fired body 20b has been determined as having no cracks by a determination means, not shown, the result is transmitted from the determination means to a distribution control means (not shown) that controls the distribution operation of the distribution mechanism 4. Here, in the distribution control means that receives the result of determination, the number of times of the transporting operations required for transporting the honeycomb fired body 20b from the position II to the position IV is stored and set to two times. Consequently, upon recognition that the honeycomb fired body 20b having no cracks has been transported to position IV after the two-times transporting operations so that the number of times of the transporting operations has reached the set value (two times), the distribution control means allows the distribution mechanism 4 to operate so as to distribute and transport the honeycomb fired body 20b to the next process, based upon the previously received result of determination indicating the existence of no cracks.

In contrast, when the determination means determines that a crack exists in the honeycomb fired body 20b, the result of determination indicating the existence of a crack is transmitted from the determination means to the distribution control means. Upon arrival of the honeycomb fired body 20b to the position IV after the two-times transporting operations, the distribution control means allows the distribution mechanism 4 to operate to exclude the honeycomb fired body 20b from the transporting line based upon the previously received result of determination indicating the existence of a crack.

In this manner, in the method for inspecting a honeycomb fired body according to an embodiment of the present invention, a four-point bending test is carried out on all the manufactured honeycomb fired bodies by using a predetermined load, and those that have not been fractured are transported to the next process as good products, while those that have been fractured are disposed of as defective products.

Here, although the four-point bending test has been explained as the inspection method in the inspection unit 10, a three-point bending test may be used, or another inspection method may be used.

The conditions of the four-point bending test are not particularly limited, and may be properly determined depending on the dimension of the honeycomb fired body. Here, the settings of the test conditions may be determined by reference to JIS R 1601. The contents of JIS R 1601 are incorporated herein by reference in its entirety.

For example, in the case of a honeycomb fired body comprising a silicon carbide sintered body having a size of 34.3 mm×34.3 mm×150 mm, the number of cells (cell density) of 46.5/cm$^2$ and a thickness of 0.25 mm in substantially all the cell walls, desirably, the span between the two pressing members 3 is set to, for example, 10 to 30 mm, the span between the two supporting members 2 is set to, for example, 120 to 140 mm, the pressing speed after the contact of the pressing members 3 to the honeycomb fired body is set to, for example, 0.1 to 5.0 mm/min, and the load applied by each pressing member 3 is set to, for example, 10 to 40 MPa.

Figure 2:
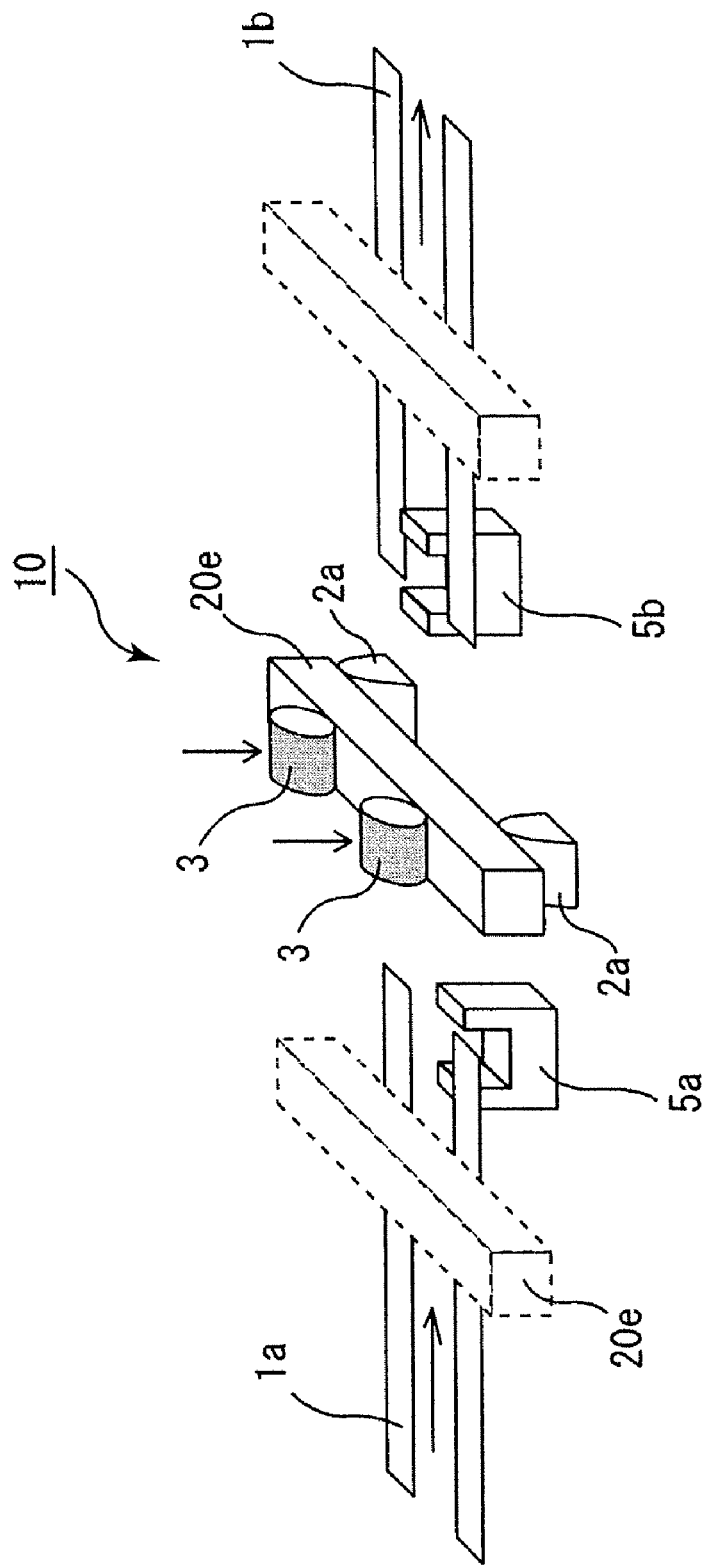
FIG. 2 is a perspective view of an inspection device which is used in a method according to another embodiment of the present invention.

The foregoing description has discussed an embodiment in which the distribution mechanism installed in the transporting member is used as the mechanism for determining and separating good products and defective products; however, not limited to this, those honeycomb fired bodies determined as defective products may be disposed of immediately after the inspection in the inspection unit. This embodiment will be discussed in the following description with reference to FIG. 2. FIG. 2 is a perspective view of an inspection device which is used in a method according to another embodiment of the present invention.

In the embodiment shown in FIG. 2, a honeycomb fired body 20e, indicated by a broken line, is transported to a position before the inspection unit 10 by using transporting members 1a placed in parallel with each other, and then a lifting means 5a rises from between the transporting members 1a to lift the honeycomb fired body 20e. Next, the lifting means 5a moves to a position above the supporting members 2a placed with a predetermined interval in between, and then descends so that the honeycomb fired body 20e is placed on the supporting members 2a.

After the placement of the honeycomb fired body 20e, the pressing members 3 are pressed onto the honeycomb fired body 20e from above with a predetermined load so that the inspection is carried out. Here, upon determination that the honeycomb fired body 20e has no cracks and is a good product, the lifting means 5b lifts the honeycomb fired body 20e, and moves above the transporting member 1b, and then descents so as to place the honeycomb fired body 20e on the transporting member 1b. Next, the honeycomb fired body 20e, which is a good product, is transported to the next process by the transporting member 1b.

In contrast, when the honeycomb fired body 20e is fractured and determined as having a crack, the fractured honeycomb fired body 20e is directly made to pass between the supporting members 2a and drop into a disposing inlet (not shown) placed below the inspection unit 10 to be disposed of. By using a distribution mechanism having this structure, it also becomes possible to separate good products and defective products efficiently.

Moreover, in the method for inspecting a honeycomb fired body according to the embodiment of the present invention, those honeycomb fired bodies determined as good products may be directly transported to the next process, or a visual inspection may be concurrently carried out thereon in the middle of the transportation. The visual inspection is effective for inspecting fine chips or the like on the surface, which would not be detected by the inspection using a device.

As described above, in the method for inspecting a honeycomb fired body according to the embodiment of the present invention, the honeycomb fired body is inspected for the presence or absence of a crack, while it is being transported continuously or intermittently by a transporting member; therefore, it is possible to carry out a total inspection of honeycomb fired bodies on the production line, while properly maintaining the production efficiency, so that those honeycomb fired bodies having no cracks and those honeycomb fired bodies having a crack can be efficiently separated from each other.

The following description will discuss a method for manufacturing a honeycomb structured body according to the embodiment of the present invention.

The method for manufacturing a honeycomb structured body comprising a honeycomb fired body includes: molding a ceramic material to manufacture a pillar-shaped honeycomb molded body having a number of cells longitudinally placed in parallel with one another with a cell wall therebetween; and firing the honeycomb molded body to manufacture a honeycomb fired body, wherein, after obtaining the honeycomb fired body, presence or absence of a crack in the honeycomb fired body is inspected, and a honeycomb fired body having no cracks is used to manufacture the honeycomb structured body.

Figure 3:
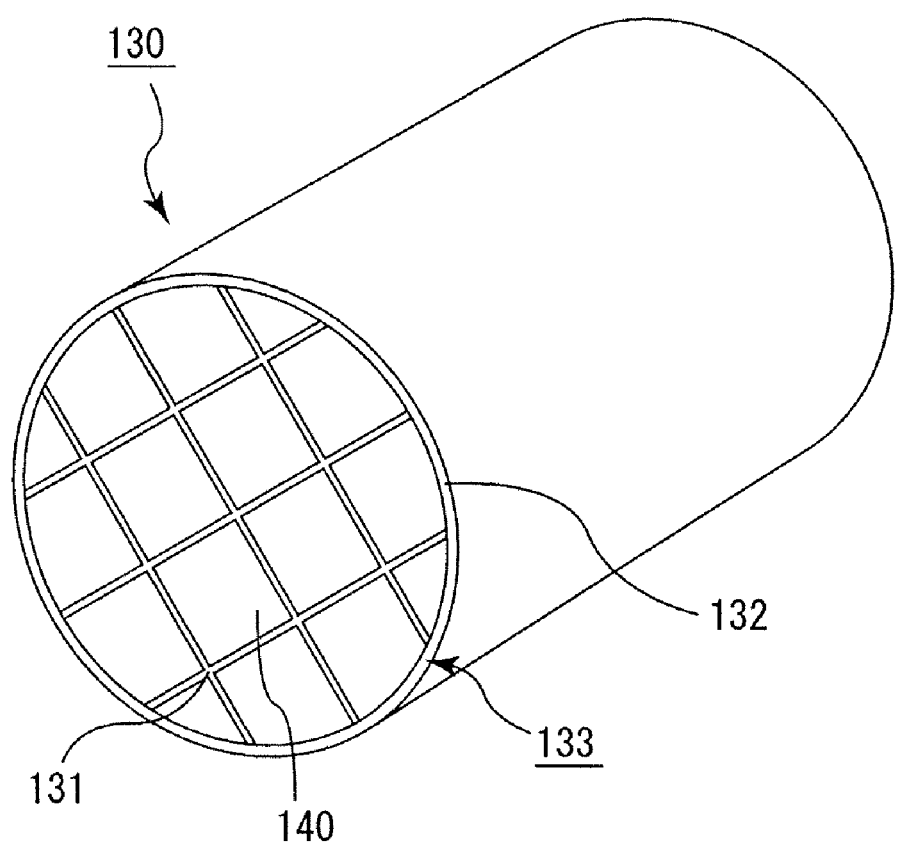
FIG. 3 is a perspective view that schematically shows one example of a honeycomb structured body.

FIG. 3 is a perspective view that schematically shows one example of a honeycomb structured body, FIG. 4(a) is a perspective view that schematically shows a honeycomb fired body forming the honeycomb structured body, and FIG. 4(b) is a cross-sectional view taken along line A-A of FIG. 4(a).

In a honeycomb structured body 130, a plurality of honeycomb fired bodies 140 shown in FIGS. 4(a) and 4(b) are combined with one another by interposing sealing material layers (adhesive layers) 131 to form a ceramic block 133, and a sealing material layer (coat layer) 132 is further formed on the outer periphery of the ceramic block 133.

Moreover, as shown in FIGS. 4(a) and 4(b), the honeycomb fired body 140 has a number of cells 141 longitudinally placed in parallel with one another (the direction shown by an arrow a in FIG. 4(a)) so that each cell wall 143 that separates the cells 141 is allowed to function as a filter.

In other words, as shown in FIG. 4(b), each of the cells 141, formed in the honeycomb fired body 140, is sealed with a plug material layer 142 at either one of ends on its exhaust gas inlet side and exhaust gas outlet side. Therefore, exhaust gases that have entered one cell 141 are discharged from another cell 141 after having always passed through each cell wall 143 that separates the cells 141; thus, when exhaust gases pass through the cell wall 143, particulates are captured by the cell wall 143 so that the exhaust gases are purified.

The following description will discuss the method for manufacturing the honeycomb structured body according to the embodiment of the present invention successively in the order of processes.

Here, the following description will describe a method for manufacturing a honeycomb structured body in which powder of silicon carbide as a ceramic material is used, by exemplifying a method for manufacturing a honeycomb structured body in which a main component of the constituent materials is silicon carbide.

Of course, the main component of constituent materials for the honeycomb structured body is not limited to silicon carbide, and other examples of the ceramic materials include: nitride ceramic materials such as aluminum nitride, silicon nitride, boron nitride and titanium nitride; carbide ceramic materials such as zirconium carbide, titanium carbide, tantalum carbide and tungsten carbide; and oxide ceramic materials such as alumina, zirconia, cordierite, mullite, and aluminum titanate, and the like.

Among these, non-oxide ceramic materials are desirably used, and in particular, silicon carbide is more desirably used. Silicon carbide is preferable because of its superior heat resistant property, mechanical strength, thermal conductivity and the like. Here, a silicon-containing ceramic material formed by blending metal silicon with the above-mentioned ceramic material, a ceramic material such as a ceramic combined by silicon or a silicate compound, and the like may also be exemplified as the constituent materials, and among these, a material in which metal silicon is blended in silicon carbide (silicon-containing silicon carbide) is desirably used.

First, inorganic powder such as silicon carbide powders having different average particle diameters as a ceramic material is dry-mixed with an organic binder to prepare a mixed powder, and a liquid plasticizer, a lubricant and water are mixed together to prepare a mixed liquid, and then the mixed powder and the mixed liquid is mixed using a wet mixing apparatus so that a wet mixture for manufacturing molded bodies is prepared.

With respect to the particle diameter of the silicon carbide powder, although not particularly limited, those which are less susceptible to shrinkage in the succeeding firing process are desirably used, and for example, mixed powder, prepared by combining 100 parts by weight of powder having an average particle diameter from 0.3 to 50 μm with 5 to 65 parts by weight of powder having an average particle diameter from 0.1 to 1.0 μm, is desirably used.

In order to adjust the pore diameter and the like of the honeycomb fired body, it is necessary to adjust the firing temperature; however, the pore diameter can be adjusted by adjusting the particle diameter of the inorganic powder.

With respect to the organic binder, not particularly limited, examples thereof include: methyl cellulose, carboxymethyl cellulose, hydroxyethyl cellulose and polyethylene glycol, and the like. Among these, methylcellulose is more desirably used.

In general, the compounding amount of the binder is desirably set to 1 to 10 parts by weight with respect to 100 parts by weight of the inorganic powder.

With respect to the plasticizer, although not particularly limited, for example, glycerin and the like may be used.

Moreover, examples of the lubricant include polyoxy alkylene-based compounds such as polyoxyethylene alkyl ether and polyoxypropylene alkyl ether, and the like, although not limited thereto.

Specific examples of the lubricant include polyoxyethylene monobutyl ether, polyoxypropylene monobutyl ether and the like.

Here, the plasticizer and the lubricant are not necessarily contained in the raw material mixture.

Upon preparing the wet mixture, a dispersant solution may be used, and with respect to the dispersant solution, examples thereof include: water, an organic solvent such as benzene, an alcohol such as methanol, and the like.

Moreover, a molding auxiliary may be added to the wet mixture.

With respect to the molding auxiliary, although not particularly limited, examples thereof include: ethylene glycol, dextrin, fatty acid, fatty acid soap, polyalcohol, and the like.

Here, a pore forming agent, such as balloons that are fine hollow spheres composed of an oxide-based ceramic material, spherical acrylic particles, graphite and the like may be added to the above-mentioned wet mixture, if necessary.

With respect to the balloons, although not particularly limited, for example, alumina balloons, glass micro-balloons, shirasu balloons, fly ash balloons (FA balloons), mullite balloons and the like may be used. Among these, alumina balloons are more desirably used.

Here, with respect to the wet mixture using silicon carbide powder prepared as described above, the temperature thereof is desirably set to 28° C. or less. When the temperature is too high, the organic binder tends to be gelatinized.

Moreover, the rate of organic components in the wet mixture is desirably set to 10% by weight or less, and the content of moisture is desirably set from 8.0 to 20.0% by weight.

The wet mixture thus prepared is transported and charged into a molding machine.

After the wet mixture is charged into the extrusion-molding machine, the wet mixture is formed into a honeycomb molded body having a predetermined shape through extrusion molding. The honeycomb molded body is cut into a predetermined length by a molded body cutting apparatus.

Next, the honeycomb molded body is dried by using a drying apparatus, such as a microwave drying apparatus, a hot-air drying apparatus, a dielectric drying apparatus, a reduced-pressure drying apparatus, a vacuum drying apparatus and a freeze drying apparatus so that a dried honeycomb molded body is manufactured.

Here, a cutting process for cutting the two ends of the honeycomb molded body thus manufactured is carried out by using a cutting apparatus so that the honeycomb molded body is cut into a predetermined length. With this arrangement, the shrinkage of the honeycomb molded body during the drying process can be ignored.

Next, a predetermined amount of plug material paste that forms plugs is filled into ends on the outlet side of a group of cells on the inlet side and ends on the inlet side of a group of cells on the outlet side, if necessary, so that predetermined cells are sealed. Upon sealing the cells, a mask for sealing is placed on the end faces (i.e., cut faces after cutting process) of the honeycomb molded body, and only the cells that need to be sealed are filled in with the plug material paste.

With respect to the plug material paste, although not particularly limited, those plug material pastes that allow the plugs manufactured through post processes to have a porosity in a range from 30 to 75% are desirably used and, for example, the same material as that used for of the above-mentioned wet mixture may be used.

The filling of the plug material paste can be carried out on demand, and when the plug material paste has been filled therein, for example, the resulting honeycomb structured body obtained through the post process is desirably used as a honeycomb filter, and in the case where no plug material paste has been filled therein, for example, the honeycomb structured body obtained through the post process is desirably used as a catalyst supporting carrier.

Next, degreasing (for example, at a temperature of 200 to 500° C.) and then firing (for example, at a temperature of 1400 to 2300° C.) are carried out on the honeycomb molded body filled in with the plug material paste under predetermined conditions so that a honeycomb fired body (see FIGS. 4(a) and 4(b)), the entire portion of which is formed by a single fired body having a plurality of cells each placed in parallel with one another with a cell wall therebetween in the longitudinal direction, with either one of the ends of each cell plugged, is manufactured.

With respect to the degreasing conditions and firing conditions of the honeycomb molded body, conventionally used conditions used upon manufacturing a filter made from of a porous ceramic material may be adopted.

Thereafter, a plurality of honeycomb fired bodies thus obtained are combined with one another by interposing sealing material layers to manufacture a honeycomb structured body.

In the method for manufacturing a honeycomb structured body according to the embodiment of the present invention, after the honeycomb fired bodies have been manufactured, the honeycomb fired bodies are inspected for the presence or absence of a crack therein, and only the honeycomb fired bodies having no cracks are combined with one another to manufacture a honeycomb structured body.

With respect to inspection methods and inspection systems used for inspecting the presence or absence of a crack in honeycomb fired bodies, the inspection method and the inspection system as explained in the method for inspecting a honeycomb fired body according to the embodiment of the present invention are desirably used.

In the method for manufacturing a honeycomb structured body according to the embodiment of the present invention, unlike a sampling inspection, a crack inspection can be carried out on all of the honeycomb fired bodies so that the presence or absence of a crack can be certainly determined totally. Moreover, since this total inspection makes it possible to manufacture a honeycomb structured body by using only the honeycomb fired bodies having no cracks, it becomes possible to certainly ensure high quality of the honeycomb structured body.

The inspection for the presence or absence of a crack in the honeycomb fired body is desirably carried out while the honeycomb fired body is being transported by the transporting member.

By adopting the above-mentioned inspection system in which the inspection can be carried out while the honeycomb fired bodies are being transported, it becomes possible to eliminate the need for installing an independent inspection process, and consequently a cost increase, reduction in productivity and the like are not caused. Moreover, unlike an inspection method in which a sampling inspection is carried out by adding an extra inspection process therefor, the crack inspection can be carried out on all of the honeycomb fired bodies while properly maintaining the production efficiency.

Moreover, the transporting member is desirably provided with a distribution mechanism so that honeycomb fired bodies having no cracks and honeycomb fired bodies having a crack are desirably separated by using the distribution mechanism.

With respect to the distribution mechanism, the aforementioned distribution mechanism can be desirably used. By using a transporting member of this kind, it becomes possible to carry out transporting, inspection and distribution of honeycomb fired bodies in a single line, and consequently, the efficiency of the manufacturing line of a honeycomb structured body can be effectively improved.

The inspection for the presence or absence of a crack may be desirably carried out by applying a predetermined load on the honeycomb fired body.

As explained in the method for inspecting a honeycomb fired body according to the embodiment of the present invention, by utilizing the significant correlation between the change in the mechanical strength and the presence or absence of a crack, it is possible to carry out the inspection only by applying a load on the honeycomb fired body, making the inspection simply and easily applicable.

In this manner, the total inspection for the presence or absence of a crack is carried out on the honeycomb fired bodies, and only the honeycomb fired bodies having no cracks are used. Next, a sealing material paste, which forms a sealing material layer (adhesive layer) is applied with a uniform thickness to each of the side faces of each honeycomb fired body that has been discriminated as having no cracks to form a sealing material paste layer, and a process of successively laminating another honeycomb fired body on the sealing material paste layer is repeated so that an aggregate of honeycomb fired bodies having a predetermined size is manufactured.

Examples of the above-mentioned sealing material paste include a material comprising an inorganic fiber and/or an inorganic particle in addition to an inorganic binder and an organic binder, for instance.

Examples of the above-mentioned inorganic binder include silica sol, alumina sol and the like, for instance. It is also acceptable to use the above alone or in combination. Among the above-mentioned inorganic binders, silica sol is preferable.

Examples of the above-mentioned organic binder include polyvinyl alcohol, methyl cellulose, ethyl cellulose, carboxymethyl cellulose and the like, for instance. It is also acceptable to use the above alone or in combination. Among the above-mentioned organic binders, carboxymethyl cellulose is preferable.

Examples of the above-mentioned inorganic fiber include a ceramic fiber or the like such as silica-alumina, mullite, alumina and silica, for instance. It is also acceptable to use the above alone or in combination. Among the above-mentioned inorganic fibers, alumina fiber is preferable.

Examples of the above-mentioned inorganic particle include carbide, nitride and the like, for instance. More concrete examples include inorganic powders comprising silicon carbide, silicon nitride, or boron nitride. It is also acceptable to use the above alone or in combination. Among the above-mentioned inorganic particle, silicon carbide, excellent in thermal conductivity, is preferable.

Moreover, it is acceptable to add a pore-forming agent such as balloons, which are micro-sized hollow spherical bodies containing oxide ceramic as component, a spherical acrylic particle, graphite and the like to the above-mentioned sealing material paste, if necessary.

The above-mentioned balloon is not particularly limited, and examples thereof may include alumina balloon, glass micro balloon, shirasu balloon, fly ash balloon (FA balloon), mullite balloon and the like. Among these, alumina balloon is preferable.

Next, this aggregate of honeycomb fired bodies is heated so that the sealing material paste layers are dried and solidified to form sealing material layers (adhesive layers).

Next, cutting is carried out on the aggregate of honeycomb fired bodies in which a plurality of honeycomb fired bodies are combined with one another by interposing sealing material layers (adhesive layers) by using a diamond cutter or the like so that a cylindrical ceramic block is manufactured.

Then, a sealing material layer (coat layer) is formed on the outer periphery of the ceramic block by using the above-mentioned sealing material paste so that a honeycomb structured body in which a sealing material layer (coat layer) is formed on the outer periphery of the cylindrical ceramic block having a structure in which a plurality of honeycomb fired bodies are combined with one another by interposing sealing material layers (adhesive layers) is manufactured.

Thereafter, a catalyst may be supported on the honeycomb structured body, if necessary. Supporting of the catalyst may be carried out on the honeycomb fired bodies before formed into an aggregate.

In the case where a catalyst is supported thereon, an alumina film having a high specific surface area is desirably formed on the surface of the honeycomb structured body, and a co-catalyst and a catalyst such as platinum are applied onto the surface of the alumina film.

Examples of methods for forming the alumina film onto the surface of the above-mentioned honeycomb structured body include a method of impregnating the honeycomb structured body with a solution of a metallic compound containing an aluminum such as $Al(NO_3)_3$ and then heating, a method of impregnating the honeycomb structured body with a solution containing an aluminum powder and then heating, and the like, for instance.

Examples of methods for supplying the co-catalyst to the above-mentioned alumina film include a method of impregnating the honeycomb structured body with a metallic compound solution containing rare earth elements or the like such as $Ce(NO_3)_3$ and then heating, and the like, for instance.

Examples of methods for supplying the catalyst to the above-mentioned alumina film include a method of impregnating the honeycomb structured body with a nitric acid solution of diammine dinitro platinum ($[Pt(NH_3)_2(NO_2)_2]HNO_3$, platinum concentration: 4.53% by weight) and the like and then heating, and the like, for instance.

It is also acceptable to supply the catalyst according to a method of supplying a catalyst to alumina particle in advance, and impregnating the honeycomb structured body with a solution containing the alumina powder that has been given the catalyst, and then heating, and the like.

Here, the above-mentioned method for manufacturing a honeycomb structured body is a method for manufacturing an aggregated honeycomb structured body having a structure in which a plurality of honeycomb fired bodies are combined with one another by interposing sealing material layers (adhesive layers), and the method for inspecting a honeycomb fired body according to an embodiment of the present invention is used in the manufacture of the aggregated honeycomb structured body.

However, the method for inspecting a honeycomb fired body according to an embodiment of the present invention may be applied not only to the manufacturing of the aggregated honeycomb structured body, but also to the manufacturing of an integral honeycomb structured body in which the cylindrical ceramic block is formed by a single honeycomb fired body. The following description will briefly discuss this embodiment.

Upon manufacturing an integral honeycomb structured body, first, a honeycomb molded body is manufactured by using the same method as the method for manufacturing an aggregated honeycomb structured body, except that the size of the honeycomb molded body to be molded through the extrusion-molding process is larger than that of the aggregated honeycomb structured body. In this method also, the honeycomb molded body can be cut by a molded body cutting apparatus so as to manufacture a honeycomb molded body.

Next, in the same manner as the manufacturing processes of the aggregated honeycomb structured body, the honeycomb molded body is dried by using a drying apparatus, such as a microwave drying apparatus, a hot-air drying apparatus, a dielectric drying apparatus, a reduced-pressure drying apparatus, a vacuum drying apparatus and a freeze drying apparatus.

Next, a cutting process for cutting the two ends of the dried honeycomb molded body is carried out.

Next, a predetermined amount of plug material paste that forms plugs is filled into ends on the outlet side of a group of cells on the inlet side and ends on the inlet side of a group of cells on the outlet side, if necessary, so that predetermined cells are sealed.

Thereafter, degreasing and firing processes are carried out in the same manner as the manufacturing processes of the aggregated honeycomb structured body so that a ceramic block is manufactured, and by forming a sealing material layer (coat layer) thereon, if necessary, an integral honeycomb structured body can be manufactured. Here, in the case where the integral honeycomb structured body is manufactured, after the ceramic block has been formed, or after a sealing material layer (coat layer) has been formed on the outer periphery of the ceramic block, the inspection for the presence or absence of a crack in the honeycomb fired body may be carried out by using the method for inspecting the honeycomb fired body according to an embodiment of the present invention.

Here, in the case of manufacturing an integral honeycomb structured body also, a catalyst may be supported thereon by using the aforementioned method, in the same manner as the method for manufacturing the aggregated honeycomb structured body. Moreover, with respect to the main constituent material for the integral honeycomb structured body, cordierite and aluminum titanate are desirably used.

In accordance with the method for manufacturing a honeycomb structured body according to an embodiment of the present invention described above, it is possible to manufacture a honeycomb structured body with high working efficiency.

Moreover, in the case where a honeycomb structured body is manufactured by using the above-mentioned method, unlike a sampling inspection, an inspecting process for a crack can be carried out on all of honeycomb fired bodies and it is possible to manufacture a honeycomb structured body by using the honeycomb fired bodies having no cracks; therefore, it becomes possible to more certainly ensure high quality of the honeycomb structured body. Furthermore, since the crack inspection can be carried out while the honeycomb structured body is being transported by a transporting member provided with a predetermined distribution mechanism, it becomes possible to carry out the crack inspection on all of the honeycomb fired bodies while maintaining a high production efficiency, without the need for separately preparing any independent inspection process.

Moreover, the foregoing explanation has been given mainly on a honeycomb structured body serving as a honeycomb filter that is used for capturing particulates in exhaust gases; however, the honeycomb structured body may also be desirably used as a catalyst supporting carrier (honeycomb catalyst) that converts exhaust gases.

EXAMPLES

The following description will discuss the present invention in more detail by means of examples; however, the present invention is not intended to be limited only by these examples.

Example 1

In this example, first, a honeycomb fired body was manufactured by using processes up to forming the honeycomb fired body according to the method for manufacturing a honeycomb structured body according to an embodiment of the present invention.

With respect to this honeycomb fired body, first, an optimal load required for a load imposing inspection in the method for inspecting a honeycomb fired body according to an embodiment of the present invention was determined.

Moreover, separately, effects of occurrence or non-occurrence of cracks in the honeycomb fired body given to the soot capturing performance were evaluated.

Furthermore, soot capturing tests were carried out on the honeycomb fired body having a crack and the honeycomb fired body having no cracks, that are separated by the method for inspecting according to an embodiment of the present invention, so that the reliability of the method for inspecting according to an embodiment of the present invention was evaluated.

(Manufacturing of Honeycomb Fired Body)

Powder of α-type silicon carbide having an average particle diameter of 10 μm (250 kg), powder of α-type silicon carbide having an average particle diameter of 0.5 μm (100 kg) and an organic binder (methyl cellulose) (20 kg) were mixed to prepare a mixed powder.

Next, separately, a lubricant (UNILUB, made by NOF Corp.) (12 kg), a plasticizer (glycerin) (5 kg) and water (65 kg) were mixed to prepare a liquid mixture, and this liquid mixture and the mixed powder were mixed by using a wet mixing machine so that a wet mixture was prepared.

At this time, the moisture content of the met mixture was 14% by weight.

Next, the wet mixture was transported to an extrusion molding machine by using a transporting device, and charged into a material charging inlet of the extrusion molding machine.

Here, the moisture content of the wet mixture immediately before it was charged into the extrusion molding machine was 13.5% by weight.

Figure 4:
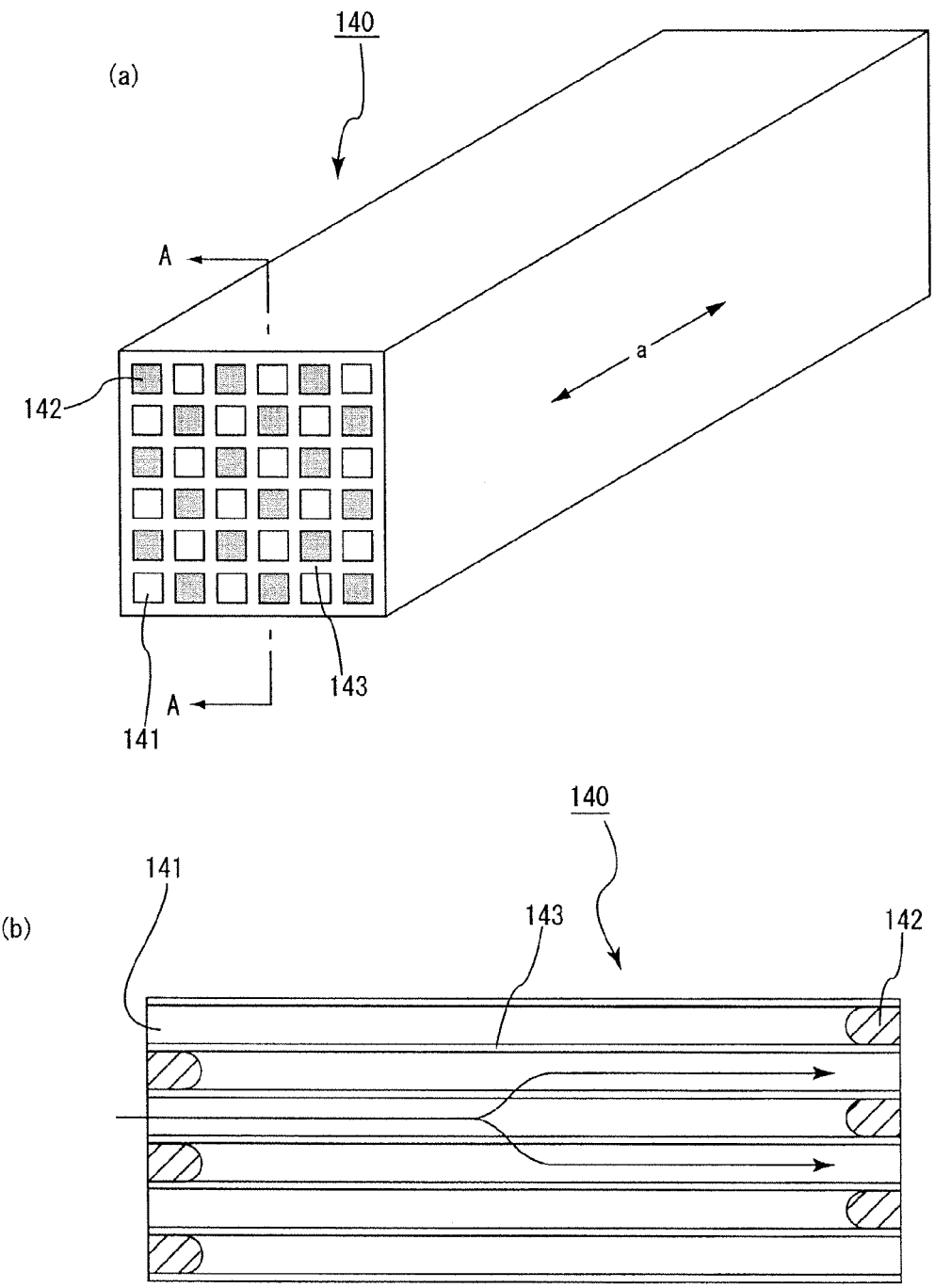
FIG. 4(a) is a perspective view that schematically shows each of honeycomb fired bodies forming the honeycomb structured body.
FIG. 4(b) is a cross-sectional view taken along line A-A of FIG. 4(a)

The wet mixture was then extrusion-molded into a molded body having a shape shown in FIG. 4.

Next, after the raw molded body had been dried by using a microwave drying apparatus or the like, a plug material paste having the same composition as the wet mixture was filled into predetermined cells.

After having been again dried by a drying apparatus, the resulting product was degreased at 400° C., and fired at 2200° C. in a normal-pressure argon atmosphere for 3 hours to manufacture a honeycomb fired body comprising a silicon carbide sintered body having a porosity of 40%, an average pore diameter of 12.5 μm, a size of 34.3 mm×34.3 mm×150 mm, the number of cells (cell density) of 46.5/cm$^2$ and a thickness of each cell wall of 0.25 mm.

(Determination of Optimal Load)

A specific sequence of processes to be used for obtaining an optimal load is described in the following (1) to (3).

(1) The honeycomb fired body thus manufactured was inspected for a crack therein by using an X-ray CT apparatus SMX-225CT (made by Shimadzu Corporation), and those honeycomb fired bodies having no cracks and those having a crack were determined and separated into respective groups.

(2) With respect to 30 pcs each of the samples of the honeycomb fired bodies having no cracks and the samples of the honeycomb fired bodies having a crack, which had been separated respectively in the above-mentioned (1), a load imposing test was carried out on those samples with each of loads shown in Table 1, and the fracture rate of the sample was obtained under the corresponding load.

(3) From the results of the load imposing test of the above (2), a range in which the fracture rate was set to 0% with respect to the honeycomb fired bodies having no cracks and at the same time the fracture rate was set to 100% with respect to the honeycomb fired bodies having a crack was obtained, and a load with which the honeycomb fired bodies having a crack would be certainly discriminated was set as an optimal load.

With respect to the load imposing test, a belt conveyor having a width of 100 mm was used as a transporting member 1 shown in FIG. 1, and a four-point bending strength test was adopted as the inspection method in the inspection unit 10. In the four-point bending strength test, a span between supporting members 2 was set to 133 mm, a span between pressing members 3 was set to 20 mm, a pressing speed was set to 0.35/min, and a load (pressure) given by each pressing member 3 was set to each of values shown in Table 1; thus, the honeycomb fired body was inspected for the presence or absence of any fracture. Load conditions and the fracture rates under those conditions were shown in Table 1.

TABLE 1

| | Good products | | Defective products | |
|---|---|---|---|---|
| Load (MPa) | Number of fractures (pcs) | Fracture rate (*) (%) | Number of fractures (pcs) | Fracture rate (*) (%) |
| 5 | 0 | 0 | 0 | 0 |
| 15 | 0 | 0 | 17 | 56.7 |
| 20 | 0 | 0 | 30 | 100.0 |
| 30 | 0 | 0 | — | — |
| 40 | 10 | 33.3 | — | — |
| 50 | 30 | 100.0 | — | — |

(*) (Number of fractures/30) × 100

Figure 5:
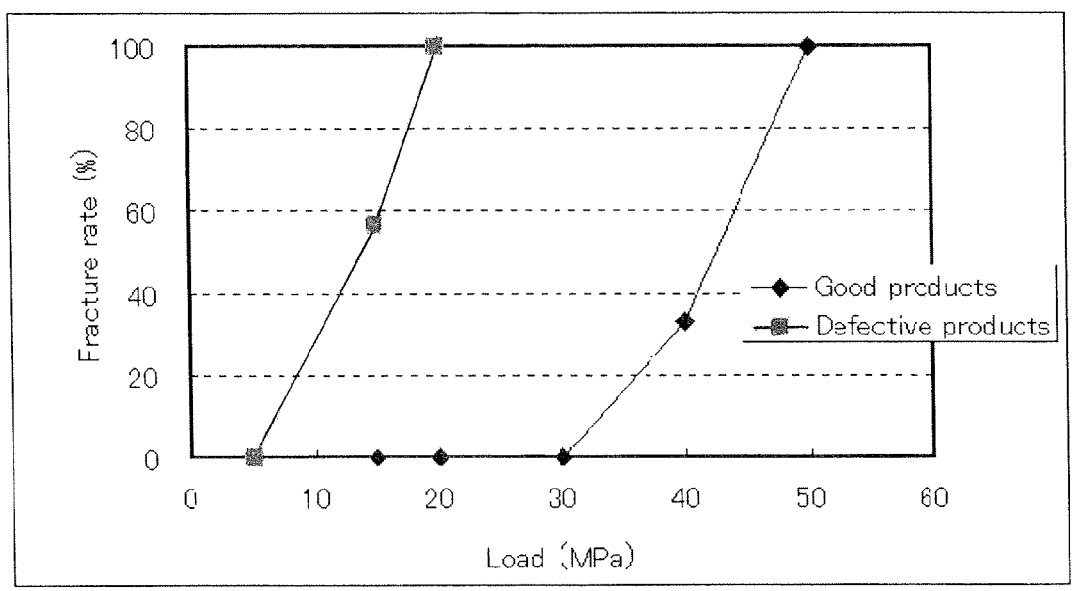
FIG. 5 is a graph that shows the relationship between a load imposed on a honeycomb fired body and the corresponding fracture rate.

From the results shown in Table 1, the relationship between the load imposed on the honeycomb fired body and the fracture rate is indicated by a graph shown in FIG. 5. The FIG. 5 is a graph indicating the relationship between the load imposed on the honeycomb fired body and the fracture rate. As shown in FIG. 5, a range of an imposed load in which the fracture rate of the honeycomb fired bodies having no cracks was 0% and at the same time the fracture rate of the honeycomb fired bodies having a crack was 100% in the present Example, was 20 to 30 MPa, and by applying a load within this range (for example, 25 MPa), it becomes possible to carry out a reliable discrimination.

With respect to the honeycomb fired body manufactured in this Example, application of the above-mentioned method makes it possible to obtain a load which fractures the honeycomb fired body when a crack exists therein, upon carrying out a load imposing test such as a four-point bending strength test thereon.

Moreover, as described above, since the optimal condition can be obtained for each of subjects of inspection, such as the size, material and cell specifications (for example, the thickness of cell walls, the number of cells, and the like) of the honeycomb fired body, it is possible to certainly discriminate honeycomb fired bodies that have a high probability of becoming defective products when used as a final product.

(Evaluation on Effects of Presence or Absence of a Crack to Soot Capturing Performance)

A soot capturing test was carried out on the honeycomb fired bodies manufactured in the present Example so as to examine what effects the presence or absence of a crack would give to the performance of the honeycomb fired bodies as a filter.

First, honeycomb fired bodies having no cracks and honeycomb fired bodies having a crack were separated in advance, and the soot capturing tests were conducted by allowing exhaust gases to flow through the respective honeycomb fired bodies.

The specific sequence of processes of the sooth capturing test is as the following (1) to (4).

(1) The honeycomb fired bodies were X-rayed by using the above-mentioned X-ray CT apparatus so that those honeycomb fired bodies having a crack and those honeycomb fired bodies having no cracks were discriminated and separated.

In a transparent image photograph of a honeycomb fired body having no cracks, existence of a crack was not confirmed over the entire portion of the honeycomb fired body; on the other hand, in a transparent image photograph of a honeycomb fired body having a crack, it was confirmed that, at two portions near the center of the honeycomb fired body, there were cracks over the entire width in a direction almost perpendicular to the longitudinal direction.

Figure 6:
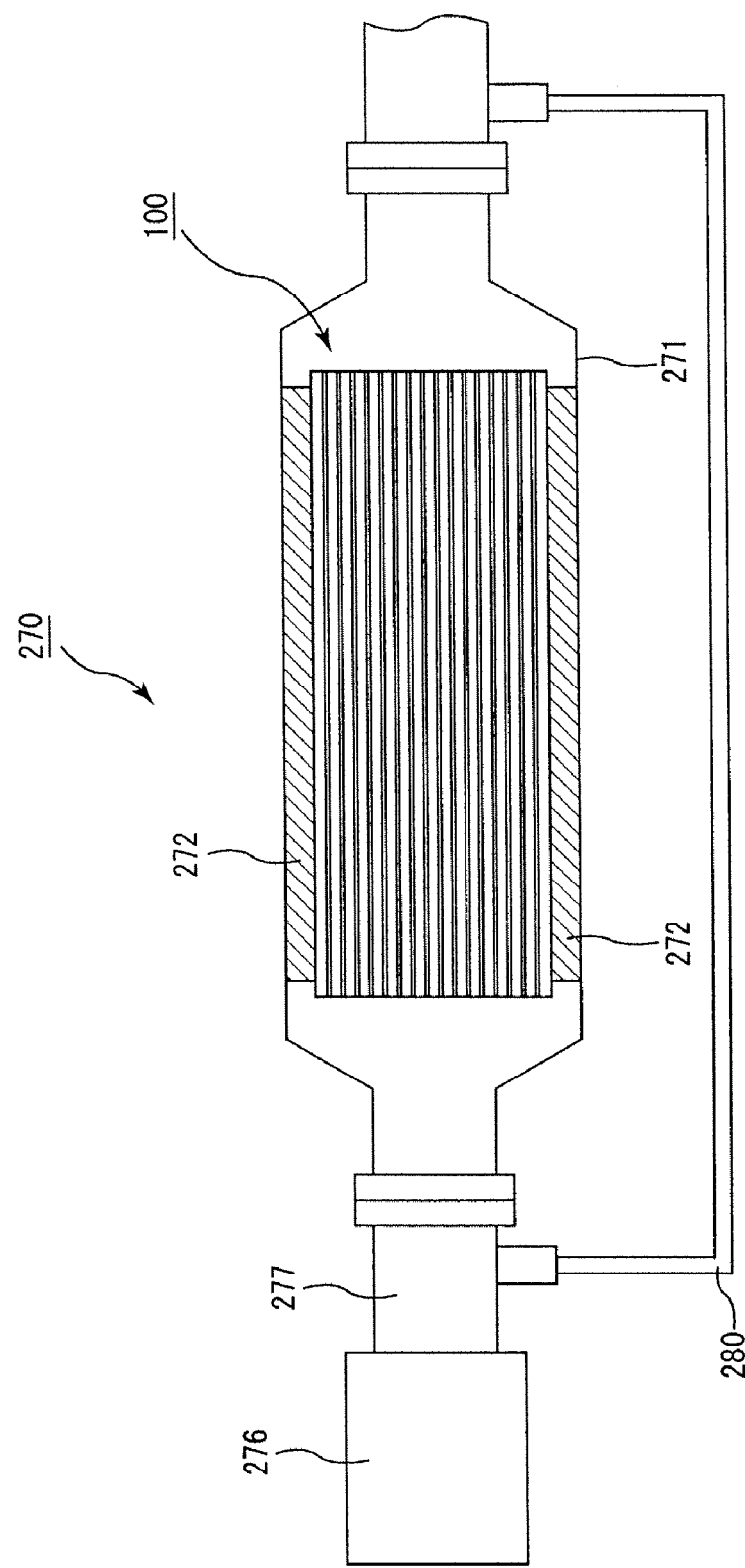
FIG. 6 is an explanatory drawing that shows a soot capturing test device.

(2) Soot capturing tests were carried out by using a sooth capturing test device 270 as shown in FIG. 6 respectively on those honeycomb fired bodies having a crack and those honeycomb fired bodies having no cracks that were discriminated by the X-ray CT apparatus. FIG. 6 is an explanatory drawing that shows the soot capturing test device.

This soot capturing test device 270 is configured by a common rail-type 2 L diesel engine 276, an exhaust gas pipe 277 that allows exhaust gases from the engine 276 to flow, a metal casing 271 that is connected to the exhaust gas pipe 277 and forms one portion of the exhaust gas pipe 277, and a pipe 280 for discharging excessive exhaust gases. The metal casing 271 is placed with a distance of about 60 cm from the engine 276, and a honeycomb fired body 100, wrapped with a 5 mm thick mat 272 made of ceramic fibers, is secured to the metal casing 271.

The soot capturing test was conducted by allowing exhaust gases from the engine 276 to flow through the honeycomb fired body 100, by driving the engine 276 at the number of revolutions of 3000 $min^{-1}$ with a torque of 50 Nm for 30 minutes.

(3) After the test, the honeycomb fired body 100 and the mat 272 were taken out of the metal casing 271, and the states of the surfaces of the honeycomb fired body 100 and the mat 272 were visually observed so that the relationship between the presence or absence of a crack in the honeycomb fired body 100 and the soot capturing performance was evaluated.

The result showed that the honeycomb fired body having no cracks was not fractured, and almost no soot adhered to the mat 272. In contrast, in the honeycomb fired body having a crack, a fracture occurred at one portion in a direction perpendicular to the longitudinal direction, and on the downstream side of the flow of exhaust gases from the position at which the fracture occurred, there was soot adhered to the mat 272, causing a blackened portion. Presumably, this was caused by soot flowing out from the fractured portion to the mat 272.

(4) Moreover, each of the honeycomb fired body having no cracks and the honeycomb fired body having a crack that had been tested was cut along the longitudinal direction, and the thickness of soot deposited on the cell wall (hereinafter, referred to also as thickness of soot deposition) was observed by an electron microscope (JSM-5900LV, made by JEOL Ltd.).

The result showed that, in the honeycomb fired body having no cracks, the thickness of soot deposition was about 60 µm; in contrast, in the honeycomb fired body having a crack, the thickness of soot deposition was much thinner.

From those results, it is presumed that soot flowed out through the fractured portion in the case of the honeycomb fired body having a crack.

In these soot capturing tests, it is presumed that the honeycomb fired bodies having a crack were fractured because they had a reduced mechanical strength, and cracks were developed due to vibration and the like of the diesel engine to cause a fracture.

As described above, when a honeycomb fired body having a crack is used as a filter, there is a high possibility of causing a problem such as a fracture during use, and a honeycomb structured body formed by combining a plurality of honeycomb fired bodies including a honeycomb fired body having a crack also has a high possibility of causing the above-mentioned problem. Therefore, in the manufacturing method according to an embodiment of the present invention, discrimination of those honeycomb fired bodies having a crack and those honeycomb fired bodies having no cracks is quite advantageous.

(Confirmation of Presence or Absence of a Crack by Using a Method for Inspecting Honeycomb Fired Body According to an Embodiment of the Present Invention)

Next, 163 pcs of the honeycomb fired bodies manufactured as described above were inspected by using the optimal load obtained as described above according to the method for inspecting a honeycomb fired body according to an embodiment of the present invention. After the inspection through the present inspection method, a soot capturing test was carried out on those honeycomb fired bodies determined as good products.

In the present inspection method, a load (pressure) given by one pressing member 3 was set to 25 MPa, and a load imposing test was carried out through the same sequence of processes as that used for obtaining the above-mentioned optimal load so that the presence or absence of a crack in the honeycomb fired body was confirmed.

The result showed that, in the present inspection method, the 163 pcs of the manufactured honeycomb fired bodies included 3 pcs of the honeycomb fired bodies having a crack (defective products) in addition to 160 pcs of the honeycomb fired bodies (good products) having no cracks.

Next, the above-mentioned soot capturing test was carried out on each of the 160 pcs of the good products.

The result showed that no soot adhesion to the mat was observed and no cracks existed in all of the corresponding honeycomb fired bodies.

In this manner, according to the method for inspecting a honeycomb fired body according to an embodiment of the present invention, it is possible to discriminate and separate those honeycomb fired bodies having a crack and those honeycomb fired bodies having no cracks efficiently and easily. Therefore, the method for manufacturing a honeycomb structured body according to an embodiment of the present invention makes it possible to reduce the occurrence of defective products in the honeycomb structured bodies after the final process, and consequently to efficiently manufacture a honeycomb structured body having a predetermined quality, while properly maintaining the production efficiency of the entire manufacturing processes.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for manufacturing a honeycomb structured body, the method comprising:
    molding a ceramic material to form a plurality of honeycomb molded bodies;
    firing the plurality of the honeycomb molded body to make a plurality of honeycomb fired bodies;
    inspecting the plurality of the honeycomb fired bodies for a crack; and
    making the honeycomb structured body using a honeycomb fired body without a crack among the plurality of the honeycomb fired bodies.

2. The method according to claim 1, wherein the honeycomb fired bodies are inspected for a crack while the honeycomb fired bodies are transported along a transportation line.

3. The method according to claim 2, wherein the honeycomb fired body without a crack and a honeycomb fired body with a crack are separated.

4. The method according to claim 3, wherein, after the honeycomb fired bodies are inspected for a crack, the honeycomb fired body with a crack is dropped from the transportation line.

5. The method according to claim 3, wherein, after the honeycomb fired bodies are inspected for a crack, the honeycomb fired body with a crack is distributed to a defective product transporting path of a Y-shaped pass and the honeycomb fired body without a crack is distributed to a non-defective product transporting path of the Y-shaped pass during the separating step.

6. The method according to claim 2, wherein the honeycomb fired bodies are so provided that longitudinal directions of the honeycomb fired bodies are substantially perpendicular to a transporting direction of the honeycomb fired bodies.

7. The method according to claim 2, wherein the honeycomb fired bodies are so provided that longitudinal directions of the honeycomb fired bodies are substantially parallel to a transporting direction of the honeycomb fired bodies.

8. The method according to claim 2, wherein the honeycomb fired bodies are transported using at least one of a belt conveyor, a chain conveyor, and a cart that travels on rails.

9. The method according to claim 2, wherein a transporting speed of the honeycomb fired bodies is at least about 5 m/min and at most about 40 m/min.

10. The method according to claim 1, wherein the honeycomb fired bodies are inspected for a crack by using at least one of a method in which a load is applied on the honeycomb fired body, a method in which a crack is detected based on a sound generated upon hitting the honeycomb fired body is utilized, a method in which a crack is detected based on differences of temperature distribution when the honeycomb fired body is heated, a method in which an X-ray image of the honeycomb fired body is taken by applying X-ray to the honeycomb fired body, a method in which vibration caused by applying ultrasonic waves to the honeycomb fired body is utilized, a method in which gas leakage is detected when a gas is flown through the honeycomb fired body, and a method in which electrodes are inserted into cells of the honeycomb fired body so as to detect a current conduction between the cells.

11. The method according to claim 1, wherein a load is applied on each of the honeycomb fired bodies to inspect the honeycomb fired bodies for a crack.

12. The method according to claim 11, wherein at least one of a three-point bending strength test and a four-point bending strength test is performed to inspect the honeycomb fired bodies for a crack.

13. The method according to claim 12, wherein a transporting member transports the honeycomb fired bodies, and wherein a width of the transporting member is shorter than a length of each of the honeycomb fired bodies in the longitudinal direction of the honeycomb fired bodies.

14. The method according to claim 11, wherein the load is so determined that the honeycomb fired body without a crack is not fractured and the honeycomb fired body with a crack is fractured by applying the load.

15. The method according to claim 1, further comprising:
providing a sealing layer between the plurality of the honeycomb fired bodies without a crack.

16. The method according to claim 1, wherein the honeycomb structured body is made from at least one of silicon carbide and silicon-containing silicon carbide.

17. The method according to claim 1, wherein the honeycomb structured body is made from the honeycomb fired body without a crack.

18. The method according to claim 17, wherein the honeycomb structured body is made from at least one of cordierite and aluminum titanate.

19. The method according to claim 1, wherein the honeycomb fired bodies and/or the honeycomb structured body carry catalyst.

20. The method according to claim 19, wherein an alumina film is formed on a surface of the honeycomb fired bodies and/or the honeycomb structured body, and wherein a co-catalyst and platinum are applied onto a surface of the alumina film.

21. The method according to claim 1, wherein the honeycomb fired bodies include an inlet cell group and an outlet cell group, and wherein outlet side ends of the inlet cell group and inlet side ends of the outlet cell group are plugged.

22. The method according to claim 1, wherein each of the plurality of the honeycomb fired body has a pillar shape having a plurality of cells separated by cell walls extending along a longitudinal direction of the pillar shape.

23. The method according to claim 1, wherein each of the plurality of the honeycomb fired body has a rectangular pillar shape.

24. The method according to claim 1, wherein each of the plurality of the honeycomb fired body is transported intermittently in the transporting step.

25. The method according to claim 1, wherein each of the plurality of the honeycomb fired body is transported continuously in the transporting step.

26. The method according to claim 1, wherein a non-contact inspection is performed in the inspecting step.

27. The method according to claim 1, wherein a contact inspection is performed in the inspecting step.

* * * * *